(12) United States Patent
Stefanchik et al.

(10) Patent No.: US 8,287,469 B2
(45) Date of Patent: Oct. 16, 2012

(54) ARTICULATING SURGICAL DEVICE AND METHOD OF USE

(75) Inventors: David Stefanchik, Morrow, OH (US); Ragae M. Ghabrial, Cincinnati, OH (US); James T. Spivey, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 884 days.

(21) Appl. No.: 11/971,410

(22) Filed: Jan. 9, 2008

(65) Prior Publication Data

US 2009/0177041 A1    Jul. 9, 2009

(51) Int. Cl.
*A61B 5/00* (2006.01)

(52) U.S. Cl. ........................................ 600/585; 600/146

(58) Field of Classification Search ................. 600/146, 600/585; 606/130
See application file for complete search history.

(56) References Cited

U.S. PATENT DOCUMENTS

| | | | |
|---|---|---|---|
| 3,470,876 A | 10/1969 | Barchilon | |
| 3,739,770 A | 6/1973 | Mori | |
| 4,454,887 A | 6/1984 | Kruger | |
| 4,520,817 A | 6/1985 | Green | |
| 4,580,551 A | 4/1986 | Siegmund et al. | |
| 5,040,715 A | 8/1991 | Green et al. | |
| 5,100,420 A | 3/1992 | Green et al. | |
| 5,211,649 A | 5/1993 | Kohler et al. | |
| 5,259,366 A | 11/1993 | Reydel et al. | |
| 5,285,795 A * | 2/1994 | Ryan et al. | 600/563 |
| 5,318,013 A | 6/1994 | Wilk | |
| 5,383,880 A | 1/1995 | Hooven | |
| 5,431,322 A | 7/1995 | Green et al. | |
| 5,433,721 A | 7/1995 | Hooven et al. | |
| 5,460,168 A | 10/1995 | Masubuchi et al. | |
| 5,482,197 A | 1/1996 | Green et al. | |
| 5,489,256 A | 2/1996 | Adair | |
| 5,518,163 A | 5/1996 | Hooven | |
| 5,518,164 A | 5/1996 | Hooven | |
| 5,618,294 A * | 4/1997 | Aust et al. | 606/170 |
| 5,624,381 A | 4/1997 | Kieturakis | |
| 5,630,782 A | 5/1997 | Adair | |

(Continued)

FOREIGN PATENT DOCUMENTS

EP    0 552 050 A2    7/1993

(Continued)

OTHER PUBLICATIONS

International Search Report, from PCT/US08/087340, mailed Apr. 6, 2009.

(Continued)

*Primary Examiner* — Rene Towa
*Assistant Examiner* — Renee Danega (57) ABSTRACT

Various embodiments of an elongate surgical device configured to travel along a tortuous body lumen to a surgical site are provided herein. In one embodiment, the device can include a tensioning element extending through a channel formed along a length of the device and the tensioning element can translate an articulation force to the working end of the device. During such articulation of the device, a portion of the channel can be configured to allow the tensioning element to exit the channel and move away from a longitudinal axis of the device thereby optimizing a mechanical advantage relative to the distal end of the device and thus maximizing the force capable of being delivered thereto. Additionally, various embodiments of a method for articulating a working end of an elongate surgical device are provided herein.

20 Claims, 9 Drawing Sheets

U.S. PATENT DOCUMENTS

| | | | |
|---|---|---|---|
| 5,651,491 | A | 7/1997 | Heaton et al. |
| 5,667,517 | A | 9/1997 | Hooven |
| 5,715,988 | A | 2/1998 | Palmer |
| 5,749,889 | A | 5/1998 | Bacich et al. |
| 5,762,256 | A | 6/1998 | Mastri et al. |
| 5,779,130 | A | 7/1998 | Alesi et al. |
| 5,782,396 | A | 7/1998 | Mastri et al. |
| 5,848,986 | A | 12/1998 | Lundquist et al. |
| 5,865,361 | A | 2/1999 | Milliman et al. |
| 5,916,147 | A | 6/1999 | Boury |
| 5,954,259 | A | 9/1999 | Viola et al. |
| 6,032,849 | A | 3/2000 | Mastri et al. |
| 6,066,090 | A | 5/2000 | Yoon |
| 6,071,233 | A | 6/2000 | Ishikawa et al. |
| 6,109,500 | A | 8/2000 | Alli et al. |
| 6,179,776 | B1 | 1/2001 | Adams et al. |
| 6,264,087 | B1 | 7/2001 | Whitman |
| 6,315,184 | B1 | 11/2001 | Whitman |
| 6,328,730 | B1 | 12/2001 | Harkrider, Jr. |
| 6,352,503 | B1 | 3/2002 | Matsui et al. |
| 6,443,973 | B1 | 9/2002 | Whitman |
| 6,468,203 | B2 | 10/2002 | Belson |
| 6,522,101 | B2 | 2/2003 | Malackowski |
| 6,569,085 | B2 | 5/2003 | Kortenbach et al. |
| 6,716,233 | B1 | 4/2004 | Whitman |
| 6,740,030 | B2 | 5/2004 | Martone et al. |
| 6,761,685 | B2 | 7/2004 | Adams et al. |
| 6,786,864 | B2 | 9/2004 | Matsuura et al. |
| 6,790,173 | B2 | 9/2004 | Saadat et al. |
| 6,793,621 | B2 | 9/2004 | Butler et al. |
| 6,793,652 | B1 | 9/2004 | Whitman et al. |
| 6,830,545 | B2 | 12/2004 | Bendall |
| 6,846,307 | B2 | 1/2005 | Whitman et al. |
| 6,846,308 | B2 | 1/2005 | Whitman et al. |
| 6,846,309 | B2 | 1/2005 | Whitman et al. |
| 6,878,106 | B1 | 4/2005 | Herrmann |
| 6,984,203 | B2 | 1/2006 | Tartaglia et al. |
| 6,997,931 | B2 | 2/2006 | Sauer et al. |
| 7,029,435 | B2 | 4/2006 | Nakao |
| 7,056,284 | B2 | 6/2006 | Martone et al. |
| 7,070,559 | B2 | 7/2006 | Adams et al. |
| 2002/0049454 | A1 | 4/2002 | Whitman et al. |
| 2002/0120253 | A1 | 8/2002 | Ouchi |
| 2003/0195387 | A1 | 10/2003 | Kortenbach et al. |
| 2003/0199736 | A1 * | 10/2003 | Christopher ............ 600/156 |
| 2004/0133075 | A1 | 7/2004 | Motoki et al. |
| 2004/0215058 | A1 | 10/2004 | Zirps et al. |
| 2004/0230095 | A1 | 11/2004 | Stefanchik et al. |
| 2004/0230096 | A1 | 11/2004 | Stefanchik et al. |
| 2004/0230097 | A1 | 11/2004 | Stefanchik et al. |
| 2005/0049460 | A1 | 3/2005 | Mikkaichi et al. |
| 2005/0080451 | A1 | 4/2005 | Griego |
| 2005/0119524 | A1 | 6/2005 | Sekine et al. |
| 2005/0119525 | A1 | 6/2005 | Takemoto |
| 2005/0124855 | A1 | 6/2005 | Jaffe et al. |
| 2005/0131278 | A1 | 6/2005 | Dickopp |
| 2005/0137454 | A1 | 6/2005 | Saadat et al. |
| 2005/0137455 | A1 | 6/2005 | Ewers et al. |
| 2005/0149067 | A1 | 7/2005 | Takemoto et al. |
| 2005/0154258 | A1 | 7/2005 | Tartaglia et al. |
| 2005/0165419 | A1 | 7/2005 | Sauer et al. |
| 2005/0177181 | A1 | 8/2005 | Kagan et al. |
| 2005/0222495 | A1 | 10/2005 | Okada et al. |
| 2005/0234297 | A1 | 10/2005 | Devierre et al. |
| 2005/0256374 | A1 | 11/2005 | Long et al. |
| 2005/0272977 | A1 | 12/2005 | Saadat et al. |
| 2006/0015009 | A1 | 1/2006 | Jaffe et al. |
| 2006/0020247 | A1 | 1/2006 | Kagan et al. |
| 2006/0079735 | A1 | 4/2006 | Martone et al. |
| 2006/0258903 | A1 | 11/2006 | Stefanchik et al. |
| 2006/0258904 | A1 | 11/2006 | Stefanchik et al. |
| 2006/0259010 | A1 | 11/2006 | Stefanchik et al. |
| 2007/0173687 | A1 | 7/2007 | Shima et al. |
| 2007/0197996 | A1 * | 8/2007 | Kraft et al. ............ 604/500 |
| 2007/0208224 | A1 | 9/2007 | Olson |
| 2007/0208364 | A1 | 9/2007 | Smith et al. |
| 2007/0221700 | A1 | 9/2007 | Ortiz et al. |
| 2007/0225562 | A1 | 9/2007 | Spivey et al. |
| 2008/0183035 | A1 | 7/2008 | Vakharia et al. |

FOREIGN PATENT DOCUMENTS

| | | |
|---|---|---|
| EP | 0552423 A2 | 7/1993 |
| EP | 0 634 144 A1 | 1/1995 |
| EP | 0 705 570 A1 | 4/1996 |
| EP | 0880338 A1 | 12/1998 |
| EP | 1284120 | 2/2003 |
| EP | 1284120 A1 | 2/2003 |
| EP | 1400214 A2 | 3/2004 |
| EP | 1402837 A1 | 3/2004 |
| EP | 1 426 012 A1 | 6/2004 |
| EP | 1459695 A1 | 9/2004 |
| EP | 1477104 | 11/2004 |
| EP | 1535565 A1 | 6/2005 |
| EP | 1582138 | 10/2005 |
| EP | 1593337 A1 | 11/2005 |
| EP | 1607050 | 12/2005 |
| GB | 2109241 A | 6/1983 |
| GB | 2272159 A | 5/1994 |
| JP | 54136780 | 10/1979 |
| JP | 2000033071 A | 2/2000 |
| JP | 2000171730 A | 6/2000 |
| JP | 2000325303 | 11/2000 |
| JP | 2002143078 A | 5/2002 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005152416 A | 6/2005 |
| JP | 2005307143 A | 11/2005 |
| WO | 97/12557 | 4/1997 |
| WO | 0048506 A1 | 8/2000 |
| WO | 00/72762 A1 | 12/2000 |
| WO | 00/72765 A1 | 12/2000 |
| WO | 02/43571 | 6/2002 |
| WO | 0243571 A2 | 6/2002 |
| WO | 03000138 A2 | 1/2003 |
| WO | 03015604 A2 | 2/2003 |
| WO | 03/077769 A1 | 9/2003 |
| WO | 2004021868 A2 | 3/2004 |
| WO | 2004034875 A2 | 4/2004 |
| WO | 2004047626 A1 | 6/2004 |
| WO | 2004052426 A2 | 6/2004 |
| WO | 2004096015 | 11/2004 |
| WO | 2004103157 A2 | 12/2004 |
| WO | 2004105593 A1 | 12/2004 |

OTHER PUBLICATIONS

International Preliminary Report on Patentability Jul. 13, 2010 for Application No. PCT/US08/087340 (7 Pages).

* cited by examiner

ARTICULATING SURGICAL DEVICE AND METHOD OF USE

FIELD OF USE

The present disclosure relates to articulation of surgical devices, in particular to articulation of a working end of a flexible, elongate surgical device.

BACKGROUND

Endoscopic surgical instruments are often preferred over traditional open surgical devices since the use of a natural orifice tends to reduce the post-operative recovery time and complications. Consequently, significant development has gone into a range of endoscopic surgical instruments that are suitable for precise placement of a working end of a tool at a desired surgical site through a natural orifice. These tools can be used to engage and/or treat tissue in a number of ways to achieve a diagnostic or therapeutic effect.

Endoscopic surgery requires that the shaft of the device be flexible while still allowing the working end to be articulated to angularly orient the working end relative to the tissue, and in some cases to be actuated to fire or otherwise effect movement of the working end. Integration of the controls for articulating and/or actuating a working end of an endoscopic device tend to be complicated by the use of a flexible shaft and by the size constraints of an endoscopic instrument. Generally, the control motions are all transferred through the shaft as longitudinal translations, which can interfere with the flexibility of the shaft. There is also a desire to lower the force necessary to articulate and/or actuate the working end of the device to a level that all or a great majority of surgeons can handle. One known solution to lower the "force-to-fire" is to use electrical motors. However, surgeons typically prefer to experience feedback from the working end to assure proper operation of the end effector. The user-feedback effects are not suitably realizable in present motor-driven devices.

Thus, there remains a need for an easy to use and reliable device and method capable of articulating a working end of an elongate, flexible surgical instrument.

SUMMARY

Devices and methods for articulating a working end of an elongate surgical device are provided. In general, the presently disclosed embodiments utilize a tensioning element (e.g., one or a plurality of cables) extending along a length of the surgical device and having a distal end engaged to a working end of the sleeve. In use, the tensioning element can be slidably disposed within the device in such a manner capable of enhancing a user's mechanical advantage over the working end of the device thereby enabling a greater amount of force to be transferred to the working end of the device during articulation. As described in detail below, in one embodiment the tensioning element can be slidably disposed within a channel formed in a wall of the device which defines an inner lumen extending along the length of the device. The channel can further include any number, configuration, and/or dimension of opening(s) in communication with the channel-defined inner lumen. In use, the opening(s) can be positioned and configured to allow the tensioning element disposed within the channel to exit the channel through the opening(s) during articulation of the device. In other words, during articulation, the tensioning element can move out of the opening and away from a longitudinal axis of the surgical device thereby creating a leverage and/or an enhanced mechanical advantage over a working end of the surgical device. Thus, the presently disclosed embodiments provide an easy to use device and method capable of enhancing the ability to articulate an elongate surgical device while also increasing the functionality and performance of the device by enhancing the user's mechanical advantage over the working end.

Various aspects of such a surgical device are provided herein. In one such aspect, the surgical device includes a flexible elongate shaft having proximal and distal ends. For example, the elongate shaft can be a sleeve having an inner lumen extending between proximal and distal end for providing access to a surgical site. The device also includes a tensioning element (e.g., one or a plurality of cables, wires, etc.) extending through a channel formed along a length of the elongate sleeve between the proximal and distal ends wherein at least a portion of the channel can be configured to allow the tensioning element to exit the channel in response to a tension applied to the tensioning element. The tensioning element can be any element capable of providing tension to the elongate shaft. For example, the tensioning element can be one or any number of cables, cords, fibers, wires, etc. As indicated above, the tensioning element can be slidably disposed within a channel extending along a length of the shaft. In an exemplary embodiment, the channel can include one or more openings formed along the channel and the opening(s) can be configured to allow a portion of the tensioning element to exit the channel through the opening during articulation of the sleeve. As will be described below, various numbers, configurations, and/or dimensions of openings can be located at virtually any position along the length of the elongate shaft and/or along the length of the channel. For example, an opening can be positioned adjacent to the distal end of the elongate shaft, the opening can be positioned along a proximal portion of the shaft, the opening can be positioned at a location proximal of the distal end of the shaft, etc. Additionally, an opening can extend along any length of the channel as desired to provide the desired mechanical advantage.

In one embodiment, the device can be configured to limit the distance the tensioning element can exit the channel thereby providing some desired degree of rigidity and/or stability to the shaft. For example, the device can include a retaining element (e.g., a cable, a wire, a suture, a sleeve, etc.) positioned (e.g., spiraled or wrapped) around the elongate shaft. More specifically, the retaining element can be positioned adjacent an opening so as to limit movement of the tensioning element away from the channel. In one embodiment, a distance between each subsequent spiral as well as the diameter of each spiral can be selected to provide a desired degree of rigidity and/or stability to the elongate shaft.

The presently disclosed device can also include an actuator coupled to the proximal end of the elongate shaft. The actuator can be configured to apply tension to the tensioning element thereby bending (or articulating) the elongate shaft in a desired configuration. Virtually any type of actuator capable of delivering tension to the tensioning element is within the spirit and scope of the present disclosure. For example, the actuator can be a movable (e.g., pivotable) handle element configured to apply an axial force to the distal end of the tensioning element. In other embodiments, the actuator can include various spool elements in communication with the tensioning element such that, for example, a first spool element can control manipulation of a first cable, and a second spool element can control manipulation of a second cable. In short, the actuator can include any type of mechanism capable of providing a force to the distal end of the tensioning element which is then capable of translating the force to the working end of the device to enable to the desired articulation.

In another aspect, a surgical device is provided which includes a flexible elongate sleeve having proximal and distal ends with an inner lumen having a longitudinal axis extending therethrough. In use, the inner lumen is configured to provide access to a surgical site for various tools or instruments. The device can also include a tensioning element (e.g., at least one cable, wire, cord, etc.) extending between the proximal and distal ends of the elongate sleeve. The tensioning element can be slidably coupled to the elongate sleeve such that a distance between the longitudinal axis of the inner lumen of the sleeve and a portion of the tensioning element can increase in response to a tension being applied to the tensioning element. As described below, such an increase in distance can provide an enhanced mechanical advantage over the working end of the device which thereby enables a greater amount of force to be transferred to the desired area of the device (e.g., the working end).

As indicated, the tensioning element can include any number of cables (e.g., 1, 2, 3, 4, etc.) extending along a length of the sleeve. For example, the tensioning element can include a first cable extending through a first channel in the elongate sleeve, and a second cable extending through a second channel in the elongate sleeve. As indicated above, each channel can be configured so as to allow the cable disposed therein to exit the channel during articulation of the sleeve. Similar to above, each channel can be formed within the elongate sleeve. Additionally, each channel can further be in communication with any number of openings (e.g., a first opening in communication with the first channel and a second opening in communication with the second channel) formed within the elongate sleeve. For example, a first opening can be configured to allow a portion of the first cable to exit the first channel therethrough, and the second opening can be configured to allow a portion of the second cable to exit the second channel therethrough. The first and second openings can have any length and can be formed at virtually any location along the length of the elongate sleeve (e.g., adjacent to the distal end of the sleeve, positioned along a proximal end, etc.). The device can also include, similar to above, a retaining element (e.g., a spiral wire) extending along a length of the device and configured to retain or limit the distance the first and the cables move away from their respective channels through their respective openings.

In yet another embodiment, the elongate surgical sleeve can be configured as an accessory channel capable of being coupled to a second elongate surgical sleeve (e.g., an endoscopic device). In such an embodiment, the elongate sleeve can include a mating element (e.g., a rail) extending along a length thereof and configured to detachably engage a corresponding mating element formed on the second flexible elongate sleeve.

Additionally, various aspects of a method of articulating a flexible elongate device are provided herein. In one such embodiment, the method includes delivering a flexible elongate device along a tortuous body lumen to a surgical site wherein the elongate device can include an inner lumen defining a longitudinal axis. The method can also include applying tension to a tensioning element (e.g., at least one cable, wire, cord, etc.) extending through the elongate device so as to increase a distance between the longitudinal axis of the device and a portion of tensioning element and thereby cause a portion of the elongate device to bend (or articulate). In one embodiment, the tensioning element can include a first cable and a second cable, and the method can further include applying tension to the first cable extending through the elongate device to increase a distance between the longitudinal axis of the device and a portion of the first cable. In use, application of such a force can cause a first portion of the elongate device to bend in a first desired orientation. Further, the method can also include applying a tension to the second cable extending through the elongate device to increase a distance between the longitudinal axis of the device and a portion of the second cable. Like above, this force can cause a second portion of the elongate device to bend in a second orientation. In another embodiment, the method can further include controlling the distance between the longitudinal axis of the device and the tensioning element by spiraling, looping, or otherwise positioning a retaining element (e.g., a cable, wire, etc.) around a portion of the elongate device. Similar to above, the retaining element can be configured to engage the tensioning element as the element moves out of an opening formed in the channel and away from the longitudinal axis of the elongate device.

The methods can also include delivering a surgical instrument to a treatment site via an inner lumen of the elongate device so as to perform some desired surgical procedure. In other embodiments, the method can include various sterilization and/or processing procedures or steps. For example, the method can include sterilizing the device (or any component thereof) after at least one use. In another example, the method can include obtaining any embodiment of the surgical device, sterilizing the device, and storing the surgical device in a sterile container.

BRIEF DESCRIPTION OF THE DRAWINGS

Exemplary embodiments of the present disclosure will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings.

Those skilled in the art will understand that the devices and methods specifically described herein and illustrated in the accompanying drawings are non-limiting exemplary embodiments and that the scope of the present disclosure is defined solely by the claims. The features illustrated or described in connection with one embodiment may be combined with the features of other embodiments. Such modifications and variations are intended to be included within the scope of the present disclosure.

Various embodiments of a device and method for controlling, manipulating, and/or articulating a working end of an elongate surgical device are provided herein. The present disclosure includes virtually any type of surgical instrument configured to travel along a tortuous body lumen to a surgical site. As described below, the device includes a tensioning element (e.g., one or any number of cables, wires, cords, etc.) extending from a proximal handle portion to a working end of the device. More specifically, the tensioning element includes a distal end engaged to a working end of the device and a proximal portion in communication with an actuator. In use, as an actuation force is supplied to the actuator, the tensioning element can move from a slackened state to a tensioned state thereby exerting a pulling force on the distal end of the device, thus causing the distal end to articulate, i.e., move in a direction away from a central axis of the device. In an exemplary embodiment, the device includes at least one channel formed in a wall thereof and extending from the proximal to distal end of the sleeve. The channel(s) can define an inner lumen which is configured to slidably receive the tensioning element along the length of the device. Further, at least a portion of each channel can be configured (e.g., by including at least one opening in communication with the inner lumen) such that the tensioning element can exit the channel at one or more regions thereof during articulation of the device. As described below, allowing the tensioning element to exit the channel and therefore move away from a longitudinal axis of the device during articulation can provide leverage and an enhanced mechanical advantage over a distal end of the device. Thus, the presently disclosed embodiments maximize an amount of force being supplied to the working end of the device thereby increasing the effectiveness and functionality of the surgical device.

Figure 1:
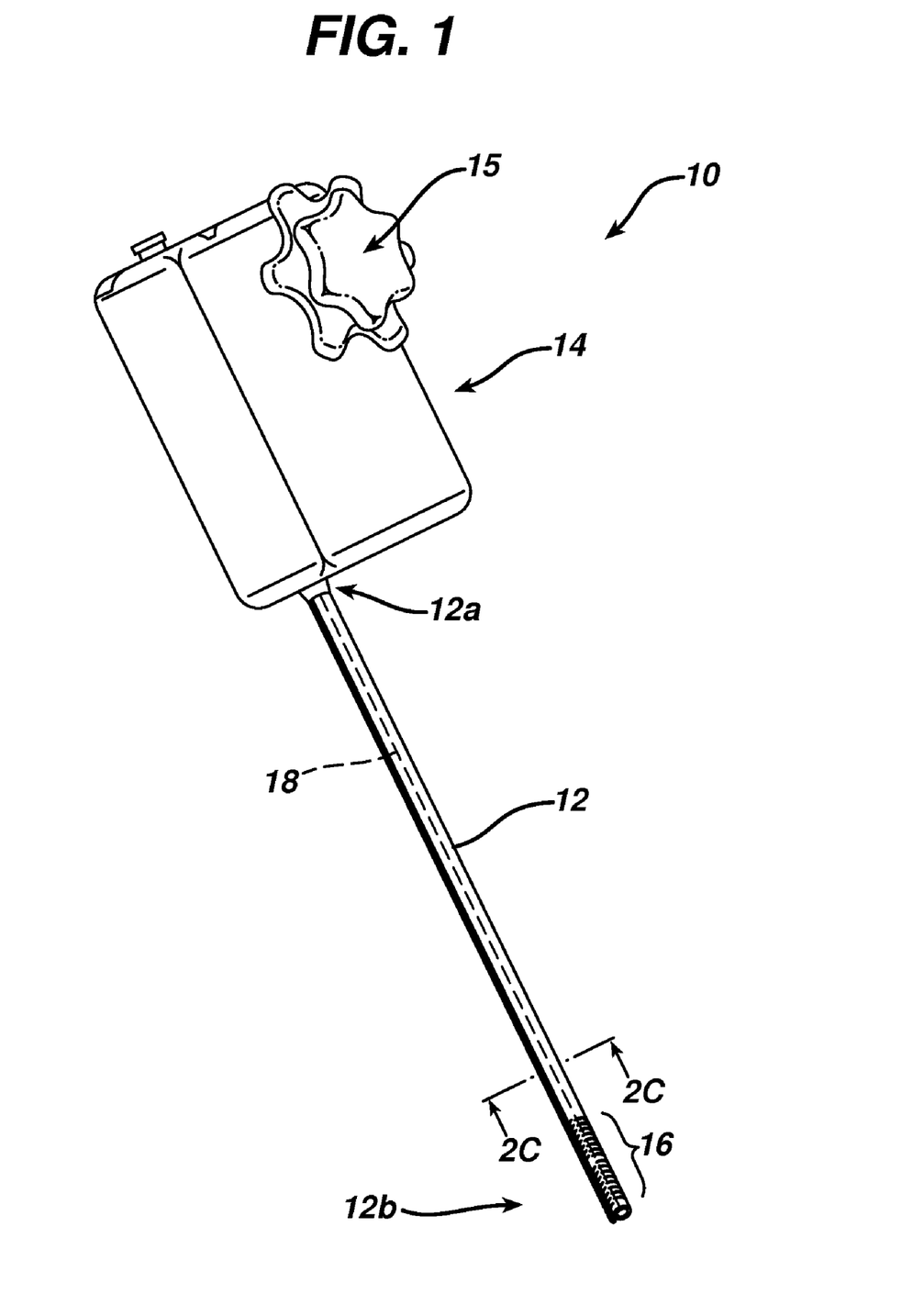
FIG. 1 is a perspective view of one exemplary embodiment of an elongate surgical device.

FIG. 1 provides one exemplary embodiment of an articulating device. As shown, the device 10 includes an elongate sleeve 12 having a proximal end 12a coupled to a handle 14 which is in communication with an actuator 15. The sleeve 12, as will be apparent to those skilled in the art, can have virtually any length and/or diameter as required for a given procedure. Additionally, while the sleeve 12 can have a generally circular cross-sectional shape, those skilled in the art will appreciate that virtually any cross-sectional shape is within the spirit and scope of the present disclosure. Additionally, the sleeve 12 can be formed from virtually any material(s) capable of providing a flexibility necessary to navigate a tortuous body lumen. In an exemplary embodiment, the sleeve 12 can include a flexible portion 16 located along a length thereof. In such an embodiment, the flexible portion 16 can have a greater flexibility as compared to the remainder of the sleeve 12 thereby facilitating articulation at the flexible portion 16. The flexible portion 16 can be formed in a variety of ways. For example, as shown in detail in FIG. 2A, the flexible portion 16 can include a number of slits 26 incorporated therein to provide enhanced flexibility. While the configuration of the slits 26 can vary, in the illustrated embodiment the slits 26 extend radially around at least a portion of the flexible portion 16, and the slits 26 are spaced axially apart from one another. Adjacent slits 26 can also be radially offset from one another. A person skilled in the art will appreciate that the location, quantity, and shape of each slit 26 can vary to obtain the desired flexibility. In other embodiments, the flexible portion 16 can have a smaller diameter as compared to the remainder of the sleeve 12 or the flexible portion 16 can be formed of a more flexible material as compared to the remainder of the sleeve 12. As will be apparent to those skilled in the art, the flexible portion 16 can be located at virtually any position along the length of the sleeve and/or the sleeve can include any number and/or length of such flexible portions 16.

Figure 2A:
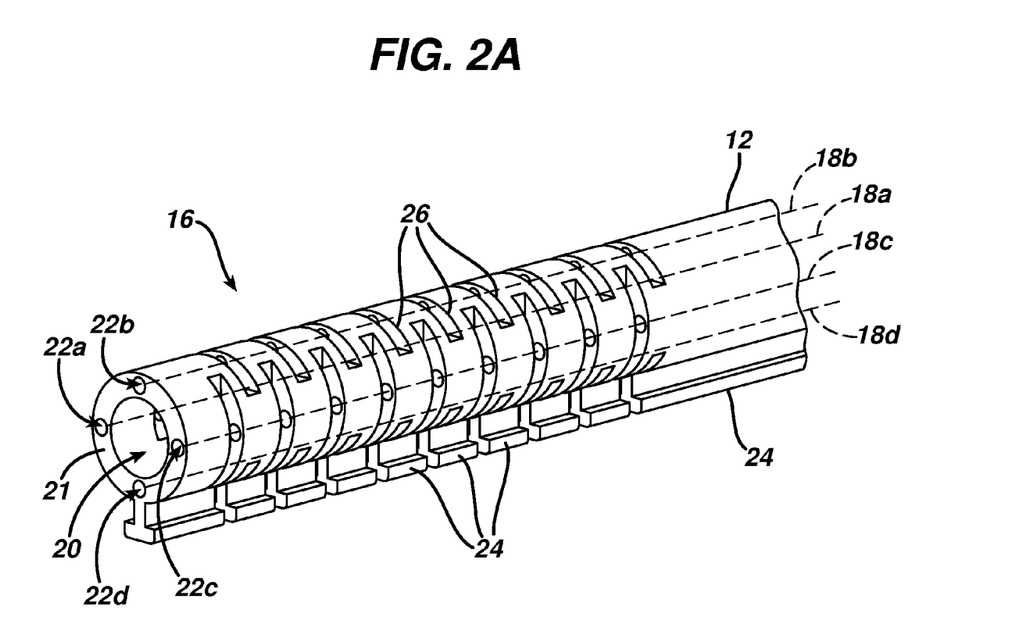
FIG. 2A is a perspective view of a distal end of the elongate surgical device of FIG. 1.
Figures 2B, 2C:
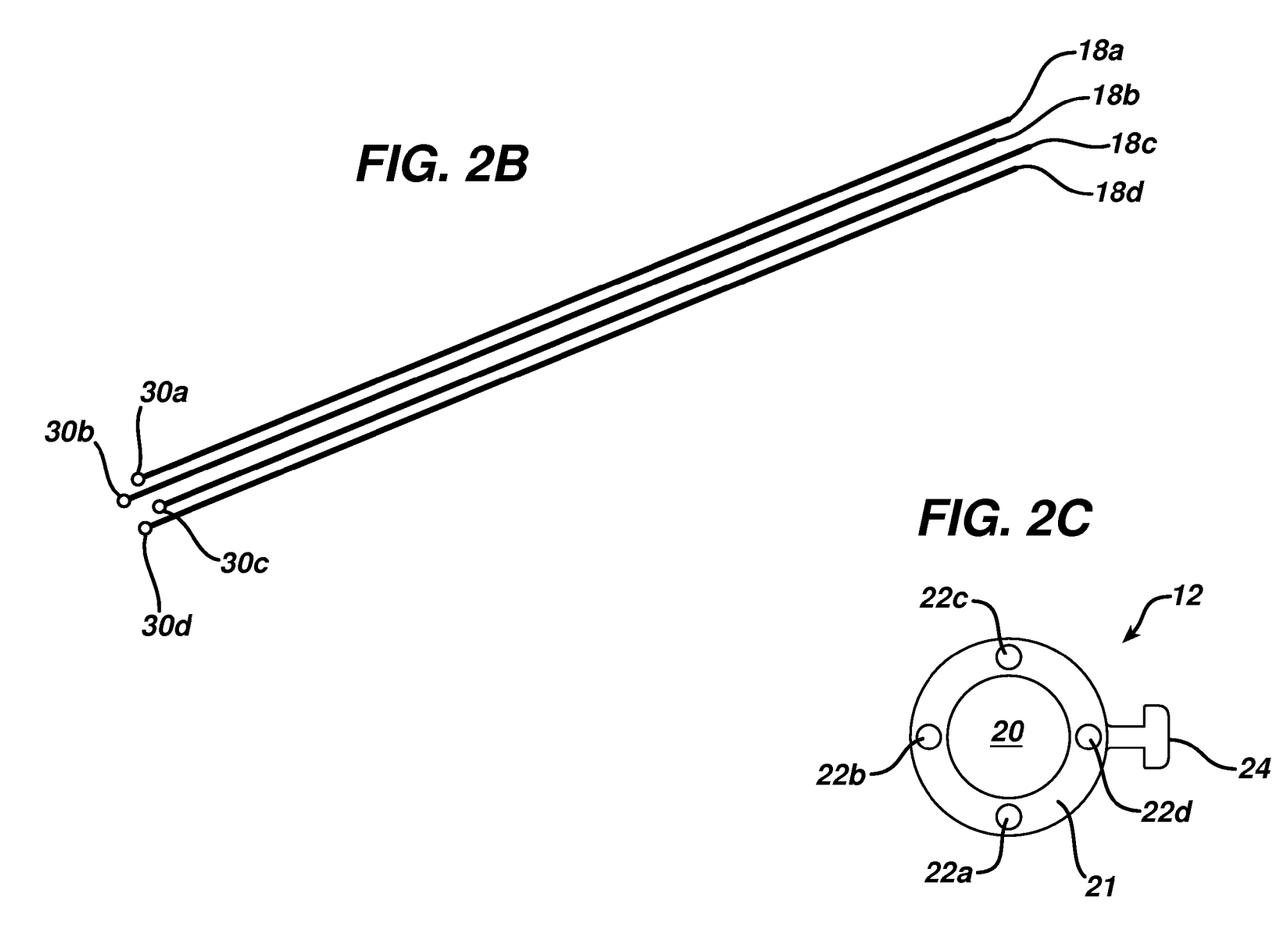
FIG. 2B is a representation of a tensioning element having a plurality of cables.
FIG. 2C is a cross-sectional view taken along line 2C-2C of the device of FIG. 1.

Looking at FIG. 2A and FIG. 2C, in an exemplary embodiment the elongate sleeve 12 can include an inner lumen 20 extending through an outer wall 21 thereby defining a longitudinal axis of the sleeve 12. In use, the inner lumen 20 can be configured to allow for delivery of various instruments and/or tools to a surgical site. For example, in one embodiment, the sleeve 12 can be an accessory sleeve having a rail 24 for mating to a second endoscopic device (such as an endoscopic sleeve, not shown). In such an embodiment, various tools can be delivered adjacent to the working end of the endoscopic device via the inner lumen 20 of the sleeve 12. The elongate sleeve 12 can also include one or a plurality of bores or channels 22a-d formed within the outer wall 21 of the sleeve 12, and each channel 22a-d can define an inner lumen extending from the distal end 12b to the proximal end 12a of the sleeve 12. As described below, the inner lumen of each channel 22a-d can be configured to slidably receive a tensioning element, such as a cable 18a-d, thereby allowing each tensioning element to extend along the entire length of the sleeve 12. Thus, as an actuation force is supplied to each cable 18a-d, the cables 18a-d can slide proximally within the corresponding channels 22a-d while translating the force to the distal end 12b of the sleeve 12. As will also be described below, the channels 22a-d can be configured such that during articulation, a maximum amount of force can be to transferred to the distal end of the sleeve 12 thereby enhancing the functionality of the device.

Figure 3A:
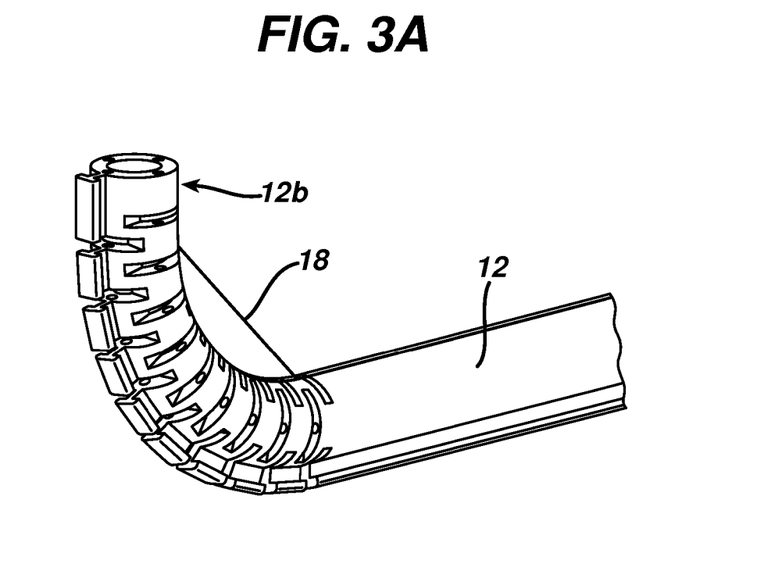
FIG. 3A is a perspective view of a distal portion of the elongate surgical device of FIG. 1 in an articulated configuration.

Referring to FIG. 1, the tensioning element 18 (shown as a dashed line) can extend between a proximal portion (e.g., a handle 14) of the device and a distal portion 12b of the sleeve 12. More specifically, the distal end of the tension element 18 can be engaged to a working end of the sleeve 12, and a proximal end or portion of the tensioning element 18 can be in communication with an actuator 15 capable of translating an actuation force to the tensioning element 18. In use, as the actuation force is supplied to the actuator 15 (discussed below), the tensioning element 18 can move from a slackened state to a tensioned state thereby exerting a pulling force on the distal end 12b of the sleeve 12 which results in some degree of articulation (see FIG. 3A) of the shaft 12. The tensioning element 18 can include virtually any type of element or mechanism capable of exerting the desired force on the distal end 12b of the sleeve 12. For example, the tensioning element 18 can include one (see FIG. 1) or a plurality (see FIG. 2A) of cables, wires, cords, etc. extending along the length of the sleeve 12. In an exemplary embodiment shown in FIG. 2A, the tensioning element includes four cables 18a-d extending along the sleeve 12 generally parallel to one another and positioned approximately 90 degrees apart from one another around a circumference of the sleeve 12. In such a configuration, applying a proximal force to cables 18a, 18c positioned about 180 degrees from one another can articulate the sleeve 12 along a first plane of movement (e.g., left and right) and applying a proximal force to a second set of cables 18b, 18d positioned about 180 degrees from one another can articulate the sleeve 12 along a second plane of movement (e.g., up and down). As will be apparent to those skilled in the art, a tensioning element having any number and/or relative positioning of cables or other wires, cords, etc. are within the spirit and scope of the present disclosure.

The tensioning element 18 can be slidably coupled to the elongate sleeve 12 in various manners. For example, as mentioned above, in an exemplary embodiment shown FIGS. 2A-2C, the elongate sleeve 12 can include various channels 22a-d formed therein with each channel 22a-d defining an inner lumen configured to receive a cable 18a-18d of the tensioning element. In general, the channels 22a-d have a cross-sectional shape substantially similar to a cross-sectional shape of a cable 18a-18d disposed therein thereby facilitating sliding of the cable 18a-18d. FIG. 2B shows a representation of four cables 18a-d relative to one another when disposed in four corresponding channels 22a-d of the elongate sleeve 12 (sleeve and channels being hidden from view). As will be apparent to those skilled in the art, the distal ends 30a-d of the cables 18a-d of the tensioning element 18 can be engaged to a desired location along the length of the corresponding channel 22a-d in virtually any manner known in the art. For example, referring to FIG. 2B, the distal end 30a-d of each cable 18a-d can include a ball or ball-like element having a larger diameter relative to a diameter of the channel 22a-d. Thus, the cables 18a-d can be sized such that in an slackened state the ends 30a-d of the cables are positioned adjacent the distal end of the sleeve 12. Thus, as the cables 18a-d are moved to a tensioned state (i.e., as an actuation force is supplied to the actuator), the ends 30a-d of the cables 18a-d can be pulled into contact with the distal end of the sleeve 12 cause the sleeve 12 to articulate away from the axis of the sleeve 12. In other embodiments, the ends 30a-d of the cables 18a-d can be glued, tied, stapled, or otherwise fixedly attached to the desired location along the corresponding channel 22a-d. Additionally, in those embodiments utilizing multiple cables 18a-d, the ends 30a-d of each cable 18a-d can be engaged at distinct locations along the length of the sleeve 12 so as to enable various additional modes of articulation. For example, in one embodiment a distal end 30a of a first cable 18a can be engaged to a distal-most end of the sleeve 12 and a distal end 30c of a second cable 18c can be engaged to the sleeve 12 at a location proximal to the distal-most end of the elongate sleeve 12. In such an embodiment, a first articulation force can be supplied to the first cable 18a and a second articulation force can be supplied to the second cable 18c thereby allowing the sleeve 12 to adopt an "S-shaped" configuration. Thus, the presently disclosed elongate surgical device can utilize a tensioning element having any number of cables with distal ends engaged to virtually any location along the length of the sleeve 12 thereby providing a wide range of possible configurations into which the sleeve 12 can be articulated or deformed.

Figure 3B:
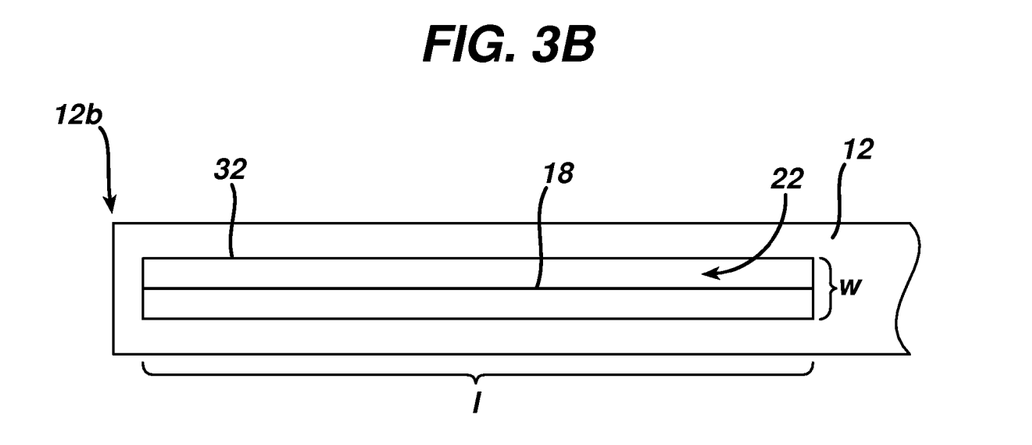
FIG. 3B is a top view of the distal portion of the device of FIG. 3A.

In an exemplary embodiment, the various channels 22a-d can be configured to allow the cables 18a-d disposed therein to achieve an enhanced mechanical advantage over a working end of the sleeve 12. For example, referring to FIGS. 3A-3B, the channel 22 can include one or a plurality of openings 32 in communication with the inner lumen of the channel 22. During articulation, the opening 32 can be configured so as to allow the tensioning element 18 to exit the channel 22 and thereby move away from a longitudinal axis of the surgical device 10. For example, looking at FIG. 3A, as the sleeve 12 is articulated (e.g., upwards), the tensioning element 18 can exit the channel 22 through the opening 32 thereby optimizing an amount of force provided by the tensioning element 18 to the distal end 12b of the sleeve 12. As will be appreciated by those skilled in the art, the opening 32 can have any length (l) and/or width (w) capable of allowing the tensioning element 18 to exit the channel 22 as desired. Further, the channel 22 can include any number of openings 32 at virtually any location along various lengths thereof. For example, the opening(s) 32 can be positioned at a distal end of the channel 22, at a location proximal to the distal end of the channel 22, at a proximal end of the channel 22, etc. Also, each channel 22 can include virtually any number of openings 32 as required to provide the desired articulation. For example, the device 10 can include a channel having a first opening formed at a location proximal to the distal end of the channel and a second opening located proximal to the first opening. Also, the device 10 can include only one channel 22 having at least one opening 32, the device can include more than one channel 22 having at least one opening 32, or each channel 22 of the device can include at least one opening 32. Thus, as will be appreciated by those skilled in the art, any such embodiment of the device 10 having any number of channels 22 with any number, orientation, position, and/or dimension of opening(s) 32 in communication with any number of the channels 22 is within the spirit and scope of the present disclosure.

Figure 4:
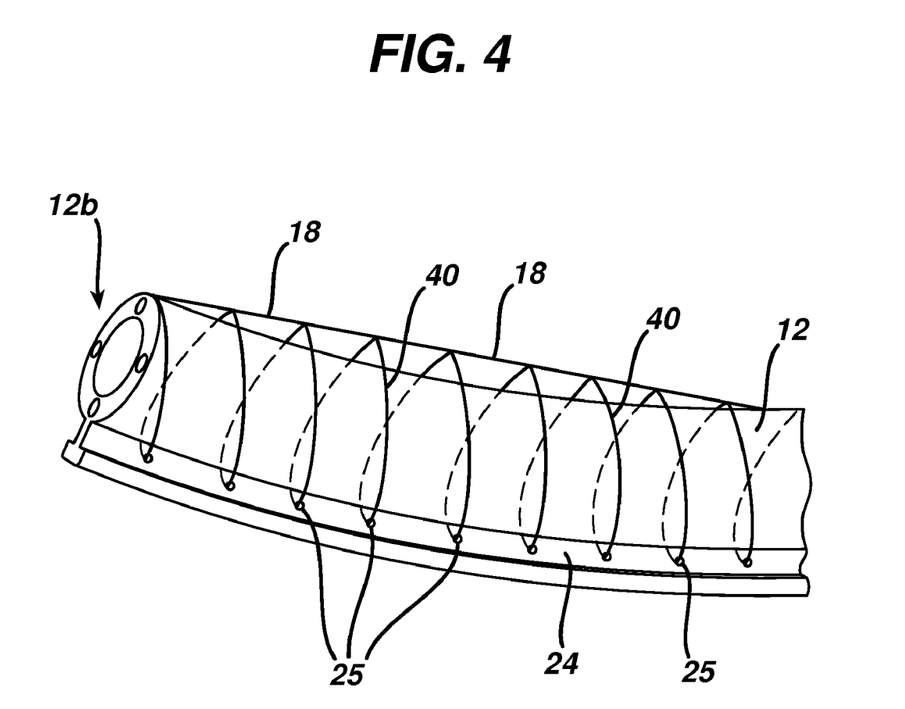
FIG. 4 is a side view of the surgical device of FIG. 1 having a retaining element spiraled around a portion of the device.

The device 10 can also be configured to limit the distance that the tensioning element 18 can exit an opening 32 of a channel 22 thereby providing a desired degree of rigidity and/or stability to the device 10. For example, as shown in FIG. 4, the device can include a retaining element 40 positioned along a length of the sleeve 12. More specifically, the retaining element 40 can be positioned adjacent an opening 32 so as to contact and thereby retain the tensioning element 18 as the tensioning element 18 exits the opening 32 of the channel 22. As will be appreciated by those skilled in the art, the retaining element 40 can be any element configured to retain and/or limit movement of the tensioning element 18 away from the longitudinal axis of the elongate shaft 12. In an exemplary embodiment, the retaining element 40 is a cable spiraled around a length of the sleeve 12. In other embodiments, the retaining element 40 can be a wire, suture, thread, sleeve, etc. As will be apparent to those skilled in the art, the retaining element 40 can extend along any desired length of the sleeve 12. Also, as will be apparent, the retaining element 40 can be a continuous cable, wire, suture, sleeve, etc., or the retaining element 40 can be discontinuous. As indicated, in an exemplary embodiment, the retaining element 40 can be spiraled around the elongate sleeve 12 of the device 10. In use, a distance between each spiral and/or a diameter of each spiral can be optimized to provide a desired degree of stability and/or rigidity. Each spiral can also be fixedly coupled to a portion of the sleeve 12 to allow each spiral to maintain a desired diameter, and to allow adjacent spirals to vary in diameter. In the embodiment shown in FIG. 4, a rail 24 extends along the shaft 12 of the device 10 and includes a plurality of openings 25 formed therein which are configured and positioned to receive each successive spiral of the retaining element 40. The spirals can be fixed within each opening using various mating techniques. Alternatively, the spirals can be slidably disposed through the openings. The spirals can also be rigid or flexible, and in some embodiments can have a predetermined shape, e.g., by forming the spirals from a shape memory material or from another material that retains its shape. In other embodiments, the retaining element 40 is spiraled around a length of the shaft 12 and not positioned through such openings 25.

Figure 5:
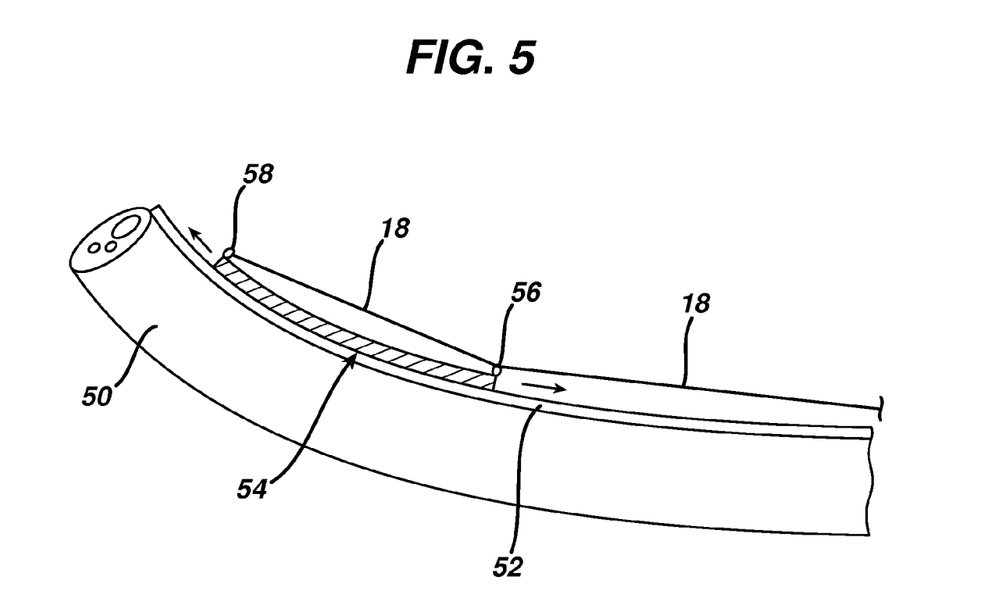
FIG. 5 is a side view of another embodiment of a surgical device having a steering assembly slidably coupled thereto.

Referring to FIG. 5, in another embodiment the device 50 (e.g., an endoscopic device) can include a steering assembly 54, and the tensioning element 18 can be engaged to a first distal ring anchor 58 (or similar such anchor) and disposed through a second proximal ring anchor 56 on the steering assembly 54 thereby allowing for articulation of the endoscopic device in response to an articulation force being applied to the tensioning element 18. Like the embodiments described above, the tensioning element 18 is once again free to move away from a longitudinal axis of the endoscopic device during articulation of the device 10 thereby enhancing a mechanical advantage relative to the distal end of the device 50. In an exemplary embodiment, the steering assembly 54 can be slidably coupled (as indicated by arrows), e.g., to a rail 52 formed along a length of the device 50. Thus, the steering assembly 54 can be moved along the length of the rail 52 so as to alter a point of articulation. As will be appreciated by those skilled in the art, the steering assembly 54 can include a locking mechanism for releasably locking the assembly 54 in a desired fixed position relative to the rail 52, and virtually any mechanism known in the art can be used.

Figure 6A:
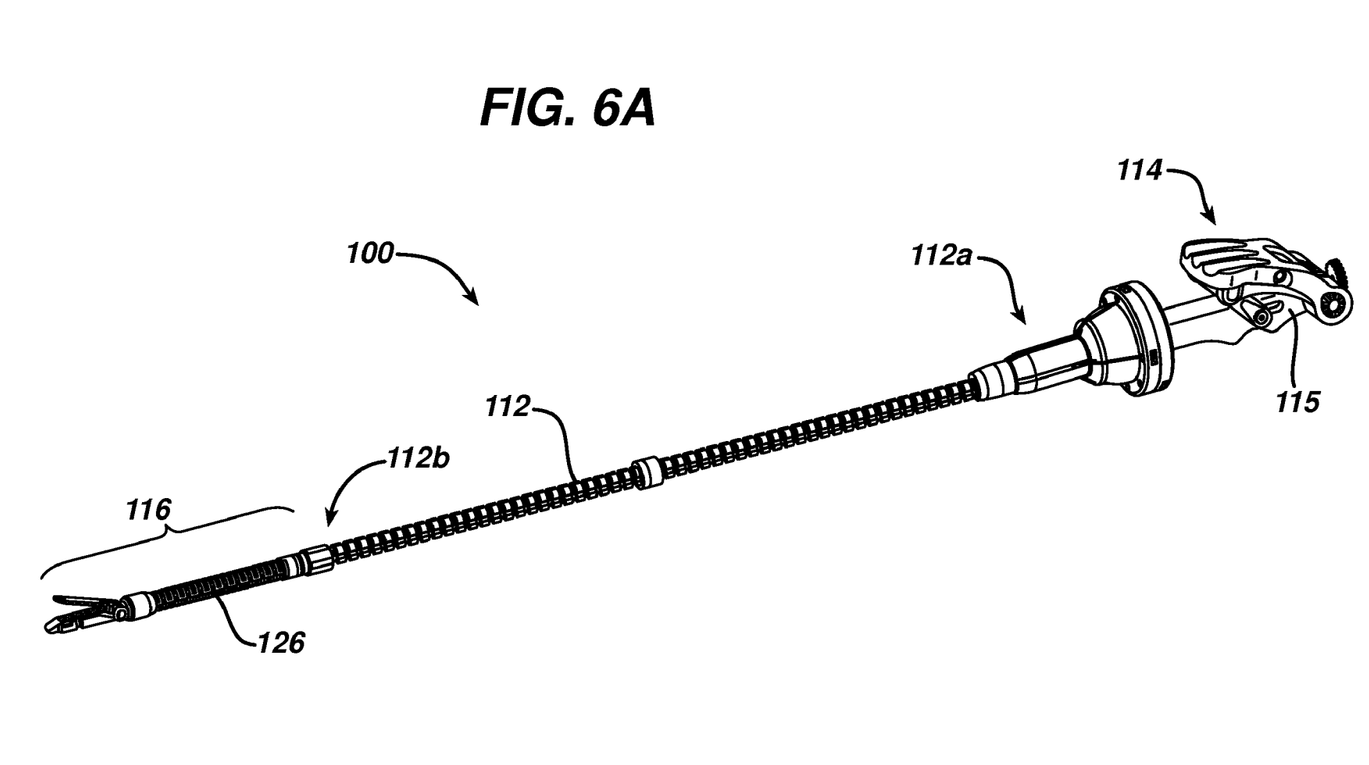
FIG. 6A is a perspective view of another embodiment of a surgical device having an end effector coupled to a distal end of an elongate shaft.
Figure 6B:
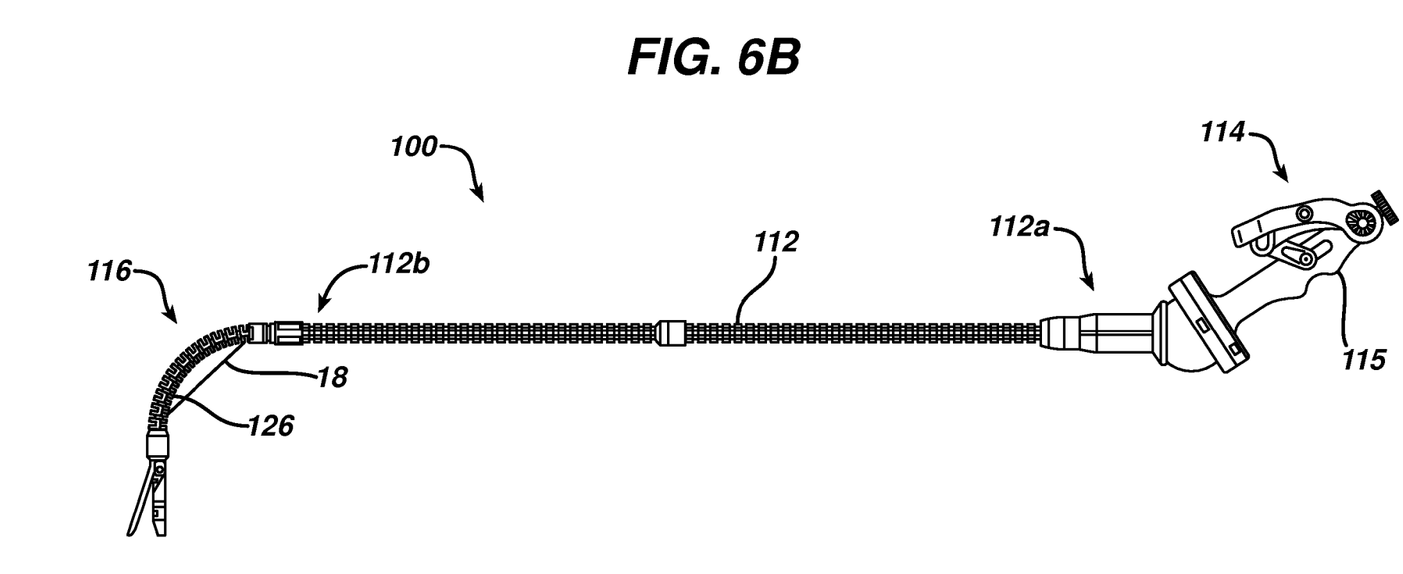
FIG. 6B is a side view of the surgical device of FIG. 6A showing the device is in an articulated configuration.

As indicated above, the surgical device can be virtually any such device capable of navigating a tortuous body lumen to a surgical site. As an alternative example, FIGS. 6A-6B provide another embodiment of a surgical device 100 having an elongate shaft 112 with a proximal end 112a coupled to a handle element 114 and a distal end 112b coupled to an end effector 116. As will be appreciated by those skilled in the art, the end effector 116 can be virtually any such end effector capable of providing a desired therapeutic function. For example, as shown, the end effector can be a surgical stapler and cutting device. Assignee's co-pending U.S. patent application Ser. No. 11/277,323, filed on Mar. 23, 2006, the entirety of which is incorporated herein be reference, provides a detailed description of such end effectors and their use with such elongate flexible sleeves.

Referring to FIG. 6B, the device 100 can, similar to the embodiments described above, include a tensioning element 18 extending from a proximal handle portion 114 (and actuator 115) to a distal end 112b of the shaft 112. The shaft 112 can also include a flexible portion 126 formed at a distal end of the device 100 thereby facilitating articulation at the flexible portion 126. The tensioning element 18 can be disposed within a channel extending from the proximal to the distal end of the device 100 and the channel can include an opening configured to allow the element 18 to exit the channel during articulation of the shaft thereby enhancing a mechanical advantage over a distal end of the device. Again, the tensioning element 18 can include any number of cables 18a-d extending along a corresponding number of channels extending along the length of the shaft 112. Additionally, each channel can include any number of openings formed therein so as to allow the tensioning element 18 to exit the channel at any desired location thereof so as to provide the desired articulation.

Figure 7:
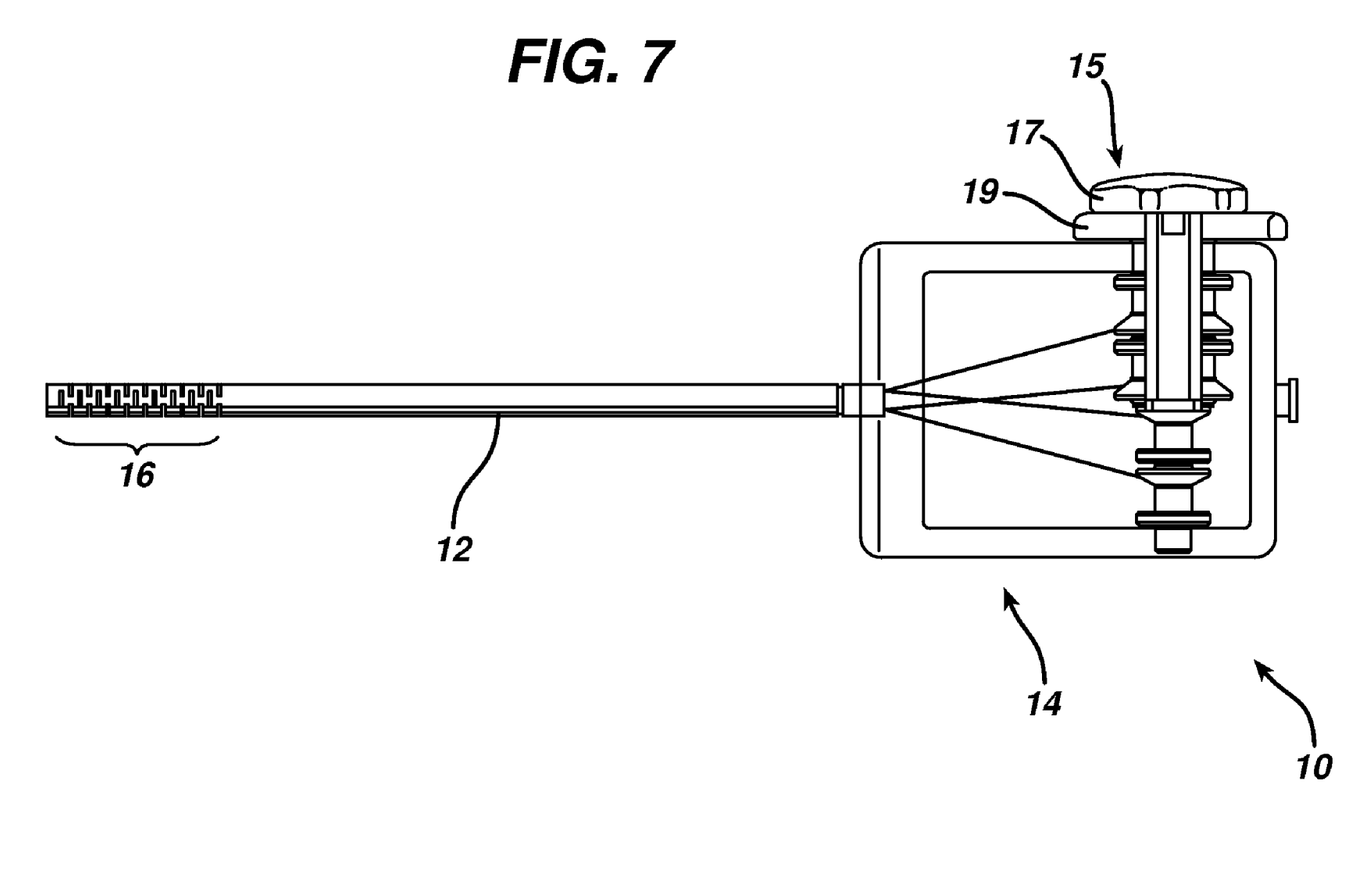
FIG. 7 is a cross-sectional view of an embodiment of a surgical device having a handle with a pulley system for articulating the device.

The various embodiments of the device described herein can include a handle coupled to a proximal end of the device. In use, the handle can be in communication with some type of actuator or actuation mechanism which is in further communication with a proximal portion of the tensioning element 18. Thus, as a user supplies an actuation force to the actuator, the tensioning element 18 can move from a slackened state to a tensioned state thereby translating a force to the distal end of the tensioning element 18 which thereby results in a desired articulation of the sleeve or shaft. As will be apparent to those skilled in the art, virtually any type of handle and/or actuator mechanism is within the spirit and scope of the present disclosure. For example, as show in FIGS. 1 and 7, the actuator 15 can include a first actuation knob 17 configured to apply a force to a first cable by rotating the knob 17 in a first direction (e.g., clockwise), and to apply a force to a second cable by rotating the knob 17 in an opposite direction (e.g., counterclockwise). In an exemplary embodiment, the first actuation knob 17 can thus control articulation along a first plane of movement (e.g., left-right) where the first and second cables extend along opposite sides of the sleeve. Further, the actuator 15 can also include a second articulation knob 19 configured to apply a force to a third cable by rotating the knob 19 in a first direction (e.g., clockwise), and to apply a force to a fourth cable by rotating the knob 19 in an opposite direction (e.g., counter-clockwise). Thus, the second articulation knob 19 can control articulation along a second plane of movement (e.g., up-down) where the third and fourth cables extend along opposite sides of the sleeve and are radially offset about 90 degrees from the first and second cables. Alternatively, FIGS. 6A-6B provide another embodiment of a handle 114 and/or actuator 115 which is movably coupled to a proximal end of the device. In use, as shown in FIG. 6B, a force can be supplied to the tensioning element 18 (thereby resulting in articulation) by pivoting the actuator 115 relative to the elongate shaft 112 of the device 100, e.g., in a direction opposite to a desired direction of articulation. A detailed description of these and other embodiments of a handle and/or actuator can be found in Assignee's co-pending U.S. patent application Ser. No. 11/277,323, filed on Mar. 23, 2006, and Assignee's co-pending U.S. patent application Ser. No. 11/762,855, filed on Jun. 14, 2007, the entirety of these disclosures being incorporated herein by reference.

Additionally, various embodiments of a method for articulating a flexible elongate sleeve are provided herein. Like above, the method can include articulating virtually any type of flexible elongate device configured to travel along a tortuous body lumen to a surgical site. For example, the elongate device can be an accessory sleeve configured to couple to a second flexible sleeve (e.g., an endoscopic device). Alternatively, the flexible elongate device can be a surgical instrument having an end effector (e.g., a surgical stapler or clip applier, graspers, cutters, coagulators, etc.) coupled to a distal end thereof. In general, the method can include delivering the flexible elongate device along a tortuous body to a surgical site. Similar to those embodiments described above, the elongate device can include an inner lumen defining a longitudinal axis. The method can also include applying tension to a tensioning element extending through the elongate device thereby articulating the device. In maximizing an amount of force supplied to the distal end of the device, the device can be configured such that a distance between the longitudinal axis of the device and a portion of tensioning element increases during articulation.

Like above, the method can include use of an elongate device having a tensioning element with any number of cables. For example, the tensioning element can include a first cable and a second cable. In such an embodiment, the method can include applying tension to the first cable which can move away from the longitudinal axis of the inner lumen of the device in response to such tension. Likewise, the method can include application of a second force or tension to the second cable which can also move away from the longitudinal axis of the device in response to articulation. In short, the method can utilize a surgical device having any number of cables, wires, cords, etc., disposed in any number of channels formed therein. Also, like above, any of the channels can include any number of openings configured to allow the tensioning element to move away from the longitudinal axis of the device during articulation. Also, the method can include controlling the distance between the longitudinal axis of the inner lumen and the tensioning element by positioning a retaining element around a portion of the elongate device such that the retainer element is configured to engage the tensioning element as the element moves away from the longitudinal axis.

The method can also include sterilizing any component of any embodiment of the device after at least one use. More specifically, the various devices disclosed herein, including portions thereof, can be designed to be disposed of after a single use, or they can be designed to be used multiple times. In either case, the device can be reconditioned for reuse after at least one use. Reconditioning can include any combination of the steps of disassembly of the device, followed by cleaning or replacement of particular pieces, and subsequent reassembly. By way of example, the elongate surgical sleeve of FIG. 1 and the surgical stapling and fastening device shown in FIGS. 6A and 6B can be reconditioned after the device has been used in a medical procedure. The device can be disassembled, and any number of the particular pieces can be selectively replaced or removed in any combination. For example, for the surgical stapling and cutting device, a cartridge disposed within the end effector and containing a plurality of fasteners can be replaced by adding a new fastener cartridge to the end effector. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the various embodiments of the device described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

One skilled in the art will appreciate further features and advantages of the present disclosure based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
a flexible elongate shaft having proximal and distal ends;
a tensioning element extending through a channel formed along a length of the elongate shaft, the channel having at least one opening configured to allow a portion of the tensioning element to exit the channel in response to a tension applied to the tensioning element and bend at least a portion of the elongate shaft, the tensioning element exiting the channel adjacent to the at least a portion of the elongate shaft that bends; and
a retaining element extending around the at least a portion of the elongate shaft that bends such that, when the retaining element is disposed around a bent portion of the elongate shaft, the retaining element allows the tensioning element at the bent portion of the elongate shaft to exit through the at least one opening, and limits displacement of the tensioning element at the bent portion of the elongate shaft.

2. The device of claim 1, wherein the shaft comprises a sleeve having an inner lumen extending between proximal and distal ends for providing access to a surgical site.

3. The device of claim 1, wherein the tensioning element is a cable.

4. The device of claim 1, further comprising an actuator coupled at the proximal end of the at least a portion of the elongate shaft, the actuator configured to apply tension to the tensioning element thereby bending the portion of the elongate shaft.

5. The device of claim 1, wherein the retaining element comprises a spiral wire.

6. The device of claim 5, wherein a diameter of the spiral wire is selected to limit a distance that the tensioning element can move out of the channel.

7. The device of claim 1, wherein the channel comprises a lumen extending through a sidewall of the elongate shaft.

8. The device of claim 7, wherein the opening is located adjacent to the distal end of the elongate shaft.

9. The device of claim 1, wherein the tensioning element includes a first cable extending through a first channel in the elongate shaft and a second cable extending through a second channel in the elongate shaft.

10. The device of claim 9, wherein the first channel comprises a first lumen extending through a sidewall of the elongate shaft having a first opening formed therein, the first opening being configured to allow a portion of the first tensioning element to exit the first channel therethrough, and the second channel comprises a second lumen extending through the sidewall of the elongate shaft having a second opening formed therein, the second opening being configured to allow a portion of the second tensioning element to exit the second channel therethrough.

11. The device of claim 10, wherein the first opening and the second opening are located adjacent to the distal end of the elongate shaft.

12. A surgical device, comprising:
a flexible elongate sleeve having proximal and distal ends with an inner lumen having a longitudinal axis extending therethrough, the inner lumen configured for delivery of surgical instruments to a surgical site;
a tensioning element extending between proximal and distal ends of the elongate sleeve and coupled to the elongate sleeve such that at least one portion of the tensioning element is configured to deflect away from the longitudinal axis of the inner lumen and extend through at least one opening on the elongate sleeve in response to a tension applied to the tensioning element; and
a retaining element spiraling around a portion of the elongate sleeve having the at least one opening, wherein a distance between each spiral is selected to limit a distance that the tensioning element extends beyond the at least one opening on the elongate sleeve.

13. The device of claim 12, further comprising a mating element extending along a length of the flexible elongate sleeve, and configured to detachably engage a mating element formed on a second flexible elongate sleeve.

14. The device of claim 12, wherein the tensioning element includes a first cable and a second cable, the first and second cables extending between the proximal and distal ends of the elongate sleeve and coupled to the elongate sleeve.

15. The device of claim 14, wherein a distal end of the first cable is mated to the elongate sleeve at a first distance proximal to the distal end of the sleeve, and a distal end of the second cable is mated to the elongate sleeve at a second distance proximal to the distal end of the sleeve and greater than the first distance.

16. A method for processing the device of claim 12 for surgery, comprising:
   a) obtaining the device of claim 12;
   b) sterilizing the device; and
   c) storing the device in a sterile container.

17. A method for articulating a flexible elongate sleeve, comprising:
   delivering a flexible elongate device having at least one opening along a tortuous body to a surgical site;
   applying tension to a tensioning element extending through the elongate device, causing a portion of the tensioning element to pass through the at least one opening and thereby bending a portion of the elongate device; and
   delivering a surgical instrument to the surgical site through the flexible elongate device;
   wherein a retaining element extends along a length of the bent portion of the elongate device and engages the tensioning element as the tensioning element moves through the at least one opening and prevents movement of the tensioning element beyond the retaining element.

18. The method of claim 17, wherein the tensioning element includes a first cable and a second cable, and the method further comprises applying tension to the first cable extending through the elongate device, causing a portion of the first cable to pass through an opening and thereby bending a first portion of the elongate sleeve in a first orientation; and applying tension to the second cable extending through the elongate device, causing a portion of the second cable to pass through an opening and thereby bending a second portion of the elongate sleeve in a second orientation.

19. The method of claim 17, further comprising delivering a surgical instrument through an inner lumen of the elongate device to a surgical site to perform a surgical procedure.

20. The method of claim 17, further comprising sterilizing the device after at least one use.

* * * * *